United States Patent [19]

Ayer

[11] 4,198,500

[45] Apr. 15, 1980

[54] TRANS-4,5-DIDEHYDRO-PGI$_1$ AMIDES

[75] Inventor: Donald E. Ayer, Kalamazoo, Mich.

[73] Assignee: The Upjohn Company, Kalamazoo, Mich.

[21] Appl. No.: 938,545

[22] Filed: Aug. 31, 1978

Related U.S. Application Data

[63] Continuation-in-part of Ser. No. 821,542, Aug. 3, 1977.

[51] Int. Cl.$^2$ ............................................. C07D 307/93
[52] U.S. Cl. ................................... 542/426; 542/418; 542/421; 542/429; 542/431; 542/432; 260/346.73
[58] Field of Search .................. 260/346.73; 542/418, 542/421, 426, 429

[56] References Cited

PUBLICATIONS

Corey et al., J.A.C.S./99:6/Mar. 1977/pp. 2006–2008.

*Primary Examiner*—Alan L. Rotman
*Assistant Examiner*—Bernard Dentz
*Attorney, Agent, or Firm*—Robert A. Armitage

[57] ABSTRACT

The present invention relates to certain structural and pharmacological analogs of prostacyclin (PGI$_2$) which are trans-4,5-didehydro-PGI$_1$ amides. These novel pharmacological agents are useful as smooth muscle stimulators.

91 Claims, No Drawings

TRANS-4,5-DIDEHYDRO-PGI$_1$ AMIDES

CROSS REFERENCE TO RELATED APPLICATION

The present application is a continuation-in-part of Ser. No. 821,542, filed Aug. 3, 1977, now pending.

The present invention provides pharmacological agents, the preparation and use of which is described in U.S. Pat. No. 4,109,082, issued Aug. 22, 1978, the relevant portion of which is incorporated here by reference. These pharmacological agents are characterized by smooth muscle stimulatory action and are related structurally to prostacyclin, being trans-4,5-didehydro-PGI$_1$ amides.

I claim:

1. A prostacyclin analog of the formula

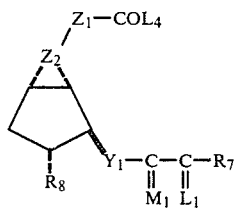

wherein $Y_1$ is trans—CH=CH—, cis—CH=CH—, or —CH$_2$CH$_2$—;
wherein $Z_2$ is

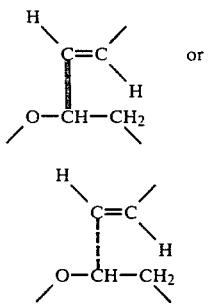

wherein $Z_1$ is
(1) —(CH$_2$)$_g$—CH$_2$—CH$_2$—, or
(2) —(CH$_2$)$_g$—CH$_2$—CF$_2$—,
wherein g is the integer zero, one, or 2;
wherein $R_8$ is hydrogen, hydroxy, or hydroxymethyl;
wherein $M_1$ is

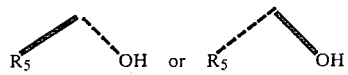

wherein $R_5$ is hydrogen or alkyl with one to 4 carbon atoms, inclusive;
wherein $L_1$ is

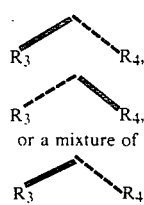
or a mixture of

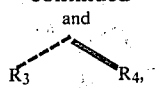

wherein $R_3$ and $R_4$ are hydrogen, methyl, or fluoro, being the same or different, with the proviso that one of $R_3$ and $R_4$ is fluoro only when the other is hydrogen or fluoro;
wherein $L_4$ is
(a) amino of the formula —NR$_{21}$R$_{22}$; wherein $R_{21}$ and $R_{22}$ are
 (i) hydrogen;
 (ii) alkyl of one to 12 carbon atoms, inclusive;
 (iii) cycloalkyl of 3 to 10 carbon atoms, inclusive;
 (iv) aralkyl of 7 to 12 carbon atoms, inclusive;
 (v) phenyl;
 (vi) phenyl substituted with one, 2, or 3 chloro, alkyl of one to 3 carbon atoms, inclusive, hydroxy, carboxy, alkoxycarbonyl of one to 4 carbon atoms, inclusive, or nitro;
 (vii) carboxyalkyl of one to 4 carbon atoms, inclusive;
 (viii) carbamoylalkyl of one to 4 carbon atoms, inclusive;
 (ix) cyanoalkyl of one to 4 carbon atoms, inclusive;
 (x) acetylalkyl of one to 4 carbon atoms, inclusive;
 (xi) benzoylalkyl of one to 4 carbon atoms, inclusive;
 (xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
 (xiii) pyridyl;
 (xiv) pyridyl substituted by one, 2, or 3 chloro, alkyl of one to 3 carbon atoms, inclusive; or alkoxy of one to 3 carbon atoms, inclusive;
 (xv) pyridylalkyl of one to 4 carbon atoms, inclusive;
 (xvi) pyridylalkyl substituted by one, 2, or 3 chloro, alkyl of one to 3 carbon atoms, inclusive, hydroxy, or alkoxy of one to 3 carbon atoms, inclusive;
 (xvii) hydroxyalkyl of one to 4 carbon atoms, inclusive;
 (xviii) dihydroxyalkyl of one to 4 carbon atoms; or
 (xix) trihydroxyalkyl of one to 4 carbon atoms;
with the further proviso that not more than one of $R_{21}$ and $R_{22}$ is other than hydrogen or alkyl;
(b) cycloamino selected from the group consisting of

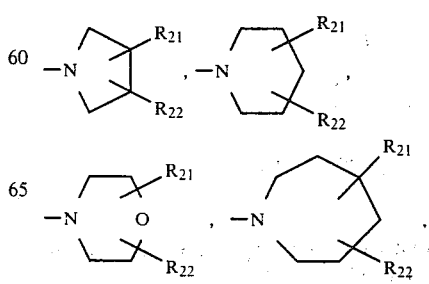

3

-continued

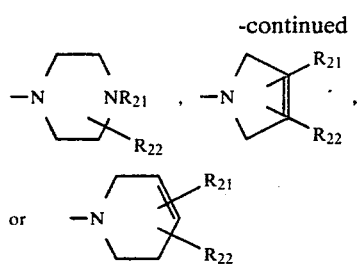

wherein $R_{21}$ and $R_{22}$ are as defined above;
(c) carbonylamino of the formula —$NR_{23}COR_{21}$, wherein $R_{23}$ is hydrogen or alkyl of one to 4 carbon atoms and $R_{21}$ is as defined above;
(d) sulfonylamino of the formula —$NR_{23}SO_2R_{21}$, wherein $R_{21}$ and $R_{23}$ are as defined above; or
(e) hydrazino of the formula —$NR_{23}R_{24}$, wherein $R_{23}$ is as defined above and $R_{24}$ is amino of the formula —$NR_{21}R_{22}$, as defined above; and
wherein $R_7$ is —$(CH_2)_m$—$CH_3$, (1)

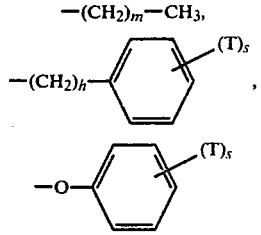 (2)

(3)

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein $Y_1$ is trans—CH=CH—.

3. A prostacyclin analog according to claim 2, wherein $Z_2$ is a mixture of

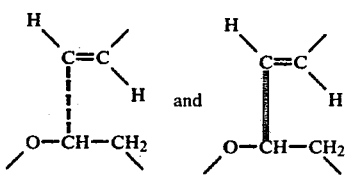

4. (6RS)-trans-4,5-didehydro-PGI$_1$, amide, a prostacyclin analog according to claim 3.

5. A prostacyclin analog according to claim 2, wherein $Z_2$ is

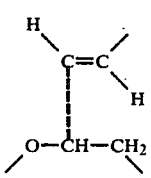

6. trans-4,5-Didehydro-6α-PGI$_1$, amide, a prostacyclin analog according to claim 5.

4

7. 15-Methyl-trans-4,5-didehydro-6α-PGI$_1$, amide, a prostacyclin analog according to claim 5.

8. 16,16-Dimethyl-trans-4,5-didehydro-6α-PGI$_1$, amide, a prostacyclin analog according to claim 5.

9. 16,16-Difluoro-trans-4,5-didehydro-6α-PGI$_1$, amide, a prostacyclin analog according to claim 5.

10. A prostacyclin analog according to claim 2, wherein $Z_2$ is

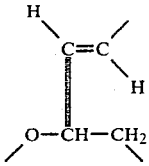

11. A prostacyclin analog according to claim 10, wherein $Z_1$ is —$(CH_2)_g$—$CH_2$—$CF_2$—.

12. 2,2-Difluoro-trans-4,5-didehydro-6β-PGI$_1$, amide, a prostacyclin analog according to claim 11.

13. A prostacyclin analog according to claim 10, wherein $Z_1$ is —$(CH_2)_g$—$CH_2$—$CH_2$—.

14. A prostacyclin analog according to claim 13, wherein g is zero.

15. A prostacyclin analog according to claim 14, wherein $R_7$ is

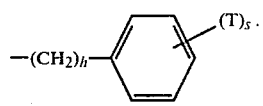

16. 17-Phenyl-18,19,20-trinor-trans-4,5-didehydro-6β-PGI$_1$, amide, a prostacyclin analog according to claim 15.

17. A prostacyclin analog according to claim 14, wherein $R_7$ is

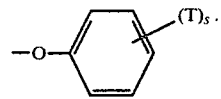

18. 16-Phenoxy-17,18,19,20-tetranor-trans-4,5-didehydro-6β-PGI$_1$, amide, a prostacyclin analog according to claim 17.

19. A prostacyclin analog according to claim 14, wherein $R_7$ is —$(CH_2)_m$—$CH_3$—.

20. A prostacyclin analog according to claim 19, wherein $R_5$ is methyl.

21. 15-Methyl-trans-4,5-didehydro-6β-PGI$_1$, amide, a prostacyclin analog according to claim 20.

22. A prostacyclin analog according to claim 19, wherein $R_5$ is hydrogen.

23. A prostacyclin analog according to claim 22, wherein at least one of $R_3$ and $R_4$ is fluoro.

24. 16,16-Difluoro-trans-4,5-didehydro-6β-PGI$_1$, amide, a prostacyclin analog according to claim 23.

25. A prostacyclin analog according to claim 22, wherein at least one of $R_3$ and $R_4$ is methyl.

26. 16,16-Dimethyl-trans-4,5-didehydro-6β-PGI$_1$, amide, a prostacyclin analog according to claim 25.

27. A prostacyclin analog according to claim 22, wherein $R_3$ and $R_4$ are both hydrogen.

28. trans-4,5-Didehydro-6β-PGI₁, methylsulfonyl amide, a prostacyclin analog according to claim 27.

29. trans-4,5-Didehydro-6β-PGI₁, piperidyl amide, a prostacyclin analog according to claim 27.

30. trans-4,5-Didehydro-6β-PGI₁, methyl amide, a prostacyclin analog according to claim 27.

31. trans-4,5-Didehydro-6β-PGI₁, amide, a prostacyclin analog according to claim 27.

32. A prostacyclin analog according to claim 1, wherein $Y_1$ is cis—CH=CH—.

33. A prostacyclin analog according to claim 32, wherein $Z_2$ is a mixture of

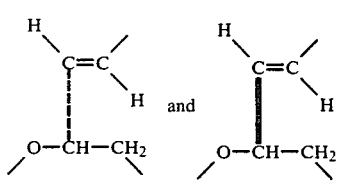

34. (6RS)-trans-4,5-didehydro-cis-13-PGI₁, amide, a prostacyclin analog according to claim 33.

35. A prostacyclin analog according to claim 33, wherein $Z_2$ is

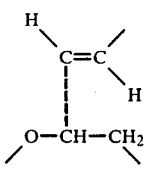

36. trans-4,5-Didehydro-cis-13-6α-PGI₁, amide, a prostacyclin analog according to claim 35.

37. 15-Methyl-trans-4,5-didehydro-cis-13-6α-PGI₁, amide, a prostacyclin analog according to claim 35.

38. 16,16-Dimethyl-trans-4,5-didehydro-cis-13-6α-PGI₁, amide, a prostacyclin analog according to claim 35.

39. 16,16-Difluoro-trans-4,5-didehydro-cis-13-6α-PGI₁, amide, a prostacyclin analog according to claim 35.

40. A prostacyclin analog according to claim 32, wherein $Z_2$ is

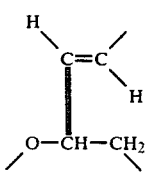

41. A prostacyclin analog according to claim 40, wherein $Z_1$ is —(CH₂)$_g$—CH₂—CF₂—.

42. 2,2-Difluoro-trans-4,5-didehydro-cis-13-6β-PGI₁, amide, a prostacyclin analog according to claim 41.

43. A prostacyclin analog according to claim 40, wherein $Z_1$ is —(CH₂)$_g$—CH₂—CH₂—.

44. A prostacyclin analog according to claim 43, wherein g is zero.

45. A prostacyclin analog according to claim 44, wherein $R_7$ is

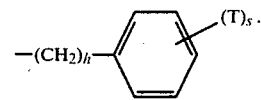

46. 17-Phenyl-18,19,20-trinor-trans-4,5-didehydro-cis-13-6β-PGI₁, amide a prostacyclin analog according to claim 45.

47. A prostacyclin analog according to claim 44, wherein $R_7$ is

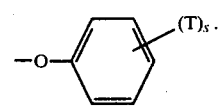

48. 16-Phenoxy-17,18,19,20-tetranor-trans-4,5-didehydro-cis-13-6β-PGI₁, amide, a prostacyclin analog according to claim 47.

49. A prostacyclin analog according to claim 44, wherein $R_7$ is —(CH₂)$_m$—CH₃—.

50. A prostacyclin analog according to claim 49, wherein $R_5$ is methyl.

51. 15-Methyl-trans-4,5-didehydro-cis-13-6β-PGI₁, amide, a prostacyclin analog according to claim 50.

52. A prostacyclin analog according to claim 49, wherein $R_5$ is hydrogen.

53. A prostacyclin analog according to claim 52, wherein at least one of $R_3$ and $R_4$ is fluoro.

54. 16,16-Difluoro-trans-4,5-didehydro-cis-13-6β-PGI₁, amide, a prostacyclin analog according to claim 53.

55. A prostacyclin analog according to claim 52, wherein at least one of $R_3$ and $R_4$ is methyl.

56. 16,16-Dimethyl-trans-4,5-didehydro-cis-13-6β-PGI₁, amide, a prostacyclin analog according to claim 55.

57. A prostacyclin analog according to claim 52, wherein $R_3$ and $R_4$ are both hydrogen.

58. trans-4,5-Didehydro-cis-13-6β-PGI₁, methylsulfonyl amide, a prostacyclin analog according to claim 57.

59. trans-4,5-Didehydro-cis-13-6β-PGI₁, piperidyl amide, a prostacyclin analog according to claim 57.

60. trans-4,5-Didehydro-cis-13-6β-PGI₁, methyl amide, a prostacyclin analog according to claim 57.

61. trans-4,5-Didehydro-cis-13-6β-PGI₁, amide, a prostacyclin analog according to claim 57.

62. A prostacyclin analog according to claim 1, wherein $Y_1$ is —CH₂CH₂—.

63. A prostacyclin analog according to claim 62, wherein $Z_2$ is a mixture of

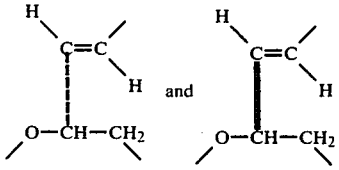

64. (6RS)-trans-4,5-didehydro-13,14-dihydro-PGI₁, amide, a prostacyclin analog according to claim 63.

65. A prostacyclin analog according to claim 63, wherein $Z_2$ is

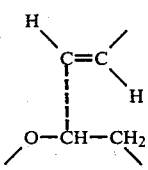

66. trans-4,5-Didehydro-13,14-dihydro-6α-PGI$_1$, amide, a prostacyclin analog according to claim 65.

67. 15-Methyl-trans-4,5-Didehydro-13,14-dihydro-6α-PGI$_1$, amide, a prostacyclin analog according to claim 65.

68. 16,16-Dimethyl-trans-4,5-didehydro-13,14-dihydro-6α-PGI$_1$, amide, a prostacyclin analog according to claim 65.

69. 16,16-Difluoro-trans-4,5-didehydro-13,14-dihydro-6α-PGI$_1$, amide a prostacyclin analog according to claim 65.

70. A prostacyclin analog according to claim 62, wherein Z$_2$ is

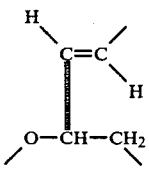

71. A prostacyclin analog according to claim 70, wherein Z$_1$ is —(CH$_2$)$_g$—CH$_2$—CF$_2$—.

72. 2,2-Difluoro-trans-4,5-didehydro-13,14-dihydro-6β-PGI$_1$, amide, a prostacyclin analog according to claim 71.

73. A prostacyclin analog according to claim 70, wherein Z$_1$ is —(CH$_2$)$_g$—CH$_2$—CH$_2$—.

74. A prostacyclin analog according to claim 73, wherein g is zero.

75. A prostacyclin analog according to claim 74, wherein R$_7$ is

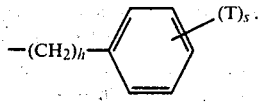

76. 17-Phenyl-18,19,20-trinor-trans-4,5-didehydro-13,14-dihydro-6β-PGI$_1$, amide a prostacyclin analog according to claim 75.

77. A prostacyclin analog according to claim 74, wherein R$_7$ is

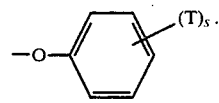

78. 16-Phenoxy-17,18,19,20-tetranor-trans-4,5-didehydro-13,14-dihydro-6β-PGI$_1$, amide, a prostacyclin analogaccording to claim 77.

79. A prostacyclin analog according to claim 74, wherein R$_7$ is —(CH$_2$)$_m$—CH$_3$—.

80. A prostacyclin analog according to claim 79, wherein R$_5$ is methyl.

81. 15-Methyl-trans-4,5-didehydro-13,14-dihydro-6β-PGI$_1$, amide, a prostacyclin analog according to claim 80.

82. A prostacyclin analog according to claim 79, wherein R$_5$ is hydrogen.

83. A prostacyclin analog according to claim 82, wherein at least one of R$_3$ and R$_4$ is fluoro.

84. 16,16-Difluoro-trans-4,5-didehydro-13,14-dihydro-6β-PGI$_1$, amide, a prostacyclin analog according to claim 83.

85. A prostacyclin analog according to claim 82, wherein at least one of R$_3$ and R$_4$ is methyl.

86. 16,16-Dimethyl-trans-4,5-didehydro-13,14-dihydro-6β-PGI$_1$, amide, a prostacyclin analog according to claim 85.

87. A prostacyclin analog according to claim 82, wherein R$_3$ and R$_4$ are both hydrogen.

88. trans-4,5-Didehydro-13,14-dihydro-6β-PGI$_1$, methylsulfonyl amide, a prostacyclin analog according to claim 87.

89. trans-4,5-Didehydro-13,14-dihydro-6β-PGI$_1$, piperidyl amide, a prostacyclin analog according to claim 87.

90. trans-4,5-Didehydro-13,14-dihydro-6β-PGI$_1$, methyl amide, a prostacyclin analog according to claim 87.

91. trans-4,5-Didehydro-13,14-dihydro-6β-PGI$_1$, amide, a prostacyclin analog according to claim 87.

* * * * *